United States Patent
Algawi et al.

(10) Patent No.: US 11,598,328 B2
(45) Date of Patent: Mar. 7, 2023

(54) DISPOSABLE PUMP CHAMBER FOR AN INFUSION PUMP

(71) Applicant: Biosense Webster (Israel) Ltd., Yokneam (IL)

(72) Inventors: Yehuda Algawi, Binyamina (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 453 days.

(21) Appl. No.: 15/481,264

(22) Filed: Apr. 6, 2017

(65) Prior Publication Data

US 2018/0291882 A1    Oct. 11, 2018

(51) Int. Cl.
*F04B 43/02* (2006.01)
*F04B 43/00* (2006.01)
(Continued)

(52) U.S. Cl.
CPC ......... *F04B 43/02* (2013.01); *A61M 5/14224* (2013.01); *F04B 43/0054* (2013.01); *F04B 53/16* (2013.01); *A61M 2005/14268* (2013.01)

(58) Field of Classification Search
CPC .. F04B 43/0009; F04B 43/0054; F04B 43/04; F04B 45/04; F04B 45/047; F04B 43/02;
(Continued)

(56) References Cited

U.S. PATENT DOCUMENTS 3,981,636 A * 9/1976 Aoki ....................... F04B 45/04
                                                        417/566
4,445,535 A   5/1984 Mayfield
(Continued)

FOREIGN PATENT DOCUMENTS

CN        101363434 A    2/2009
CN        102439316 A    5/2012
(Continued)

OTHER PUBLICATIONS

International Search Report and Written Opinion for International Application No. PCT/IB2018/051697, dated Jun. 6, 2018, 9 pages.
(Continued)

*Primary Examiner* — Bryan M Lettman
(74) *Attorney, Agent, or Firm* — Etan S. Chatlynne; Calderon Safran & Cole, P.C.

(57) ABSTRACT

An apparatus, including a pump body having an internal shaft, and a piston disposed within the shaft and having a piston head that includes a first ferromagnetic element. The apparatus also includes a motor coupled to drive a reciprocal longitudinal motion of the piston within the shaft, and a pump chamber configured to be removably attached to the pump body and having a rigid wall defining a fluid inlet, a fluid outlet, and an aperture. The apparatus additionally includes a flexible diaphragm fixed across the aperture and having a second ferromagnetic element, which engages the first ferromagnetic element when the pump chamber is attached to the pump body so that the reciprocal longitudinal motion of the piston causes alternating stretching and contraction of the flexible diaphragm, thereby modifying a volume of the pump chamber.

6 Claims, 3 Drawing Sheets

(51) Int. Cl.
*A61M 5/142* (2006.01)
*F04B 53/16* (2006.01)

(58) Field of Classification Search
CPC ......... F04B 53/16; A61M 2005/14268; A61M 5/14224
See application file for complete search history.

(56) References Cited

U.S. PATENT DOCUMENTS

| | | | |
|---|---|---|---|
| 4,768,547 A | 9/1988 | Danby et al. | |
| 4,856,340 A | 8/1989 | Garrison | |
| 5,391,199 A | 2/1995 | Ben-Haim | |
| 5,392,653 A | 2/1995 | Zanger et al. | |
| 5,443,489 A | 8/1995 | Ben-Haim | |
| 5,540,568 A | 7/1996 | Rosen et al. | |
| 5,558,091 A | 9/1996 | Acker et al. | |
| 5,944,022 A | 8/1999 | Nardella et al. | |
| 5,983,126 A | 11/1999 | Wittkampf | |
| 6,171,081 B1* | 1/2001 | Nakajima | F02M 37/046 417/470 |
| 6,172,499 B1 | 1/2001 | Ashe | |
| 6,177,792 B1 | 1/2001 | Govari et al. | |
| 6,456,864 B1 | 9/2002 | Swanson et al. | |
| 6,690,963 B2 | 2/2004 | Ben-Haim et al. | |
| 6,749,587 B2 | 6/2004 | Flaherty | |
| 6,788,967 B2 | 9/2004 | Ben-Haim et al. | |
| 7,427,281 B2 | 9/2008 | Uber, III | |
| 7,753,880 B2 | 7/2010 | Malackowski | |
| 8,827,945 B2 | 9/2014 | Baker et al. | |
| 8,834,408 B2 | 9/2014 | Baker et al. | |
| 8,915,879 B2 | 12/2014 | Smith et al. | |
| 2004/0149126 A1* | 8/2004 | Weinberger | F04B 53/22 92/128 |
| 2009/0162214 A1 | 6/2009 | Bonner | |
| 2011/0071465 A1 | 3/2011 | Wang et al. | |
| 2012/0051956 A1* | 3/2012 | Grip | F04B 53/22 417/413.1 |
| 2014/0161644 A1* | 6/2014 | Weatherley | F04B 43/021 417/360 |
| 2015/0101679 A1* | 4/2015 | Forrest | F16K 43/00 137/237 |
| 2016/0051740 A1* | 2/2016 | Wegener | A61M 1/1055 417/53 |
| 2016/0076529 A1* | 3/2016 | Kaufmann | F04B 43/02 417/472 |
| 2016/0235913 A1 | 8/2016 | Smith et al. | |
| 2018/0014878 A1* | 1/2018 | Govari | A61B 18/1206 |

FOREIGN PATENT DOCUMENTS

| | | |
|---|---|---|
| JP | 2016093756 A | 5/2016 |
| JP | 2016140766 A | 8/2016 |

OTHER PUBLICATIONS

Chinese Patent Search Record for Chinese Aplication No. 2018800376181, dated Nov. 24, 2021, 2 Pages.

* cited by examiner

DISPOSABLE PUMP CHAMBER FOR AN INFUSION PUMP

FIELD OF THE INVENTION

The present invention relates generally to infusion pumps used in medical procedures, and specifically to a diaphragm pump having a removable disposable pump chamber.

BACKGROUND OF THE INVENTION

Various therapeutic procedures such as cardiac ablation use an invasive medical probe that is inserted into a patient's body. However, during an ablation procedure on a heart, there may be local overheating of the heart surface being ablated, as well as of the heart tissue underlying the surface. The surface overheating may be manifested as charring, and the overheating of the underlying tissue may cause other damage to the tissue, even leading to penetration of the tissue. To prevent the tissue from charring, an infusion pump may deliver, via the medical probe, irrigation fluid to the region being ablated.

U.S. Pat. No. 8,834,408 to Baker et al., whose disclosure is incorporated herein by reference, describes an irrigation and/or aspiration device having a base with a removable head, and adapted for partial or complete separation of the irrigation and aspiration functions. The device includes a reservoir that is removable, replaceable and refillable.

U.S. Pat. No. 4,445,535 to Mayfield et al., whose disclosure is incorporated herein by reference, describes an infusion device that provides a precise infusion rate of a liquid medication into a body. The infusion device includes a permanent portion and a disposable portion which includes a reservoir filled with a liquid medication that is to be dispensed, and a pump for pumping the medication from the reservoir into the body.

U.S. Pat. No. 4,856,340 to Garrison, whose disclosure is incorporated herein by reference, describes a pressure diaphragm for a medication infusion system. The pressure diaphragm can be installed in a disposable cassette for use on a main pump unit, and can be configured to enable pressure downstream of a fluid pump to be measured with a high degree of accuracy.

U.S. Pat. No. 5,540,568 to Rosen et al., whose disclosure is incorporated herein by reference, describes a single module that includes a head, a rolling diaphragm filling unit, and intake and discharge ports. The rolling diaphragm filling unit may be fixed or removably attached to the head. The head module, including the intake and discharge ports, and the attached rolling diaphragm, may be configured as a disposable module that includes all of the pump surfaces that come into contact with the fluid product.

U.S. Pat. No. 6,749,587 to Flaherty, whose disclosure is incorporated herein by reference, describes a single module that includes a head, a disposable rolling diaphragm filling unit, and intake and discharge ports. The rolling diaphragm filling unit may be fixed or removably attached to the head.

U.S. Pat. No. 6,749,587 to Flaherty, whose disclosure is incorporated herein by reference, describes a modular infusion device for delivering fluid that includes a disposable assembly having an exit port assembly, and a reusable assembly having a control portion. The assemblies are adapted to be removably attached, and a power source is contained in the disposable assembly for providing power to the reusable assembly upon attachment of the reusable assembly and the disposable assembly.

U.S. Pat. No. 7,427,281 to Uber, III, whose disclosure is incorporated herein by reference, describes an injection apparatus for delivering fluid to multiple patients. The apparatus includes a first fluid source, a second fluid source, and a fluid path disposed between the first and second fluid sources and a patient. The fluid path includes a mixing device, a reusable portion for delivering fluid to multiple patients and a per-patient disposable portion removably connected to the reusable portion.

U.S. Pat. No. 7,753,880 to Malackowski, whose disclosure is incorporated herein by reference, describes a tool system for operating an irrigation pump that includes a fixed pump head driven by a pump motor and a removable tube set.

U.S. Pat. No. 8,827,945 to Baker et al., whose disclosure is incorporated herein by reference, describes irrigation and/or aspiration devices that may be configured to aspirate and irrigate alone, sequentially, or concurrently. The devices may include reservoirs for aspirant and irrigant that are removable, and/or replaceable, and/or refillable, and easily cleanable.

U.S. Pat. No. 8,915,879 to Smith et al., whose disclosure is incorporated herein by reference, describes an ambulatory infusion pump that can dispense medicament from a single-dose cartridge.

U.S. Patent Application 2016/0235913 to Smith et al., whose disclosure is incorporated herein by reference, describes ambulatory infusion pumps and reservoir assemblies that include dynamic and static seals, plus related components as well as component combinations.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention, an apparatus including a pump body having an internal shaft, a piston disposed within the shaft and having a piston head including a first ferromagnetic element, a motor coupled to drive a reciprocal longitudinal motion of the piston within the shaft, a pump chamber configured to be removably attached to the pump body and including a rigid wall defining a fluid inlet, a fluid outlet, and an aperture, and a flexible diaphragm fixed across the aperture and including a second ferromagnetic element, which engages the first ferromagnetic element when the pump chamber is attached to the pump body so that the reciprocal longitudinal motion of the piston causes alternating stretching and contraction of the flexible diaphragm, thereby modifying a volume of the pump chamber.

In one embodiment, the first ferromagnetic element includes a permanent magnet, and the second ferromagnetic element includes a metal with ferromagnetic properties. In another embodiment, the first ferromagnetic element includes a metal with ferromagnetic properties, and the second ferromagnetic element includes a permanent magnet. In an additional embodiment, the first and the second ferromagnetic elements include respective permanent magnets. In a further embodiment, at least one of the ferromagnetic elements includes an electromagnet.

In some embodiments, the apparatus may also include a medical irrigation system coupled to the motor, and a processor configured to control the medical irrigation system. In embodiments including the medical irrigation system and the processor, the apparatus may include an irrigation catheter coupled to the fluid outlet.

In further embodiments, the pump chamber is disposable. In supplemental embodiments, a pump defined by the pump chamber and the flexible diaphragm is self-priming.

There is also provided, in accordance with an embodiment of the present invention, a method including providing a pump body having an internal shaft, providing a piston disposed within the shaft and having a piston head including a first ferromagnetic element, coupling, to the piston, a motor in order to drive a reciprocal longitudinal motion of the piston within the shaft, providing a pump chamber configured to be removably attached to the pump body and including a rigid wall defining a fluid inlet, a fluid outlet, and an aperture, and affixing, across the aperture, a flexible diaphragm including a second ferromagnetic element, which engages the first ferromagnetic element when the pump chamber is attached to the pump body so that the reciprocal longitudinal motion of the piston causes alternating stretching and contraction of the flexible diaphragm, thereby modifying a volume of the pump chamber.

There is additionally provided, in accordance with an embodiment of the present invention, an apparatus including a pump body having an internal shaft, a piston disposed within the shaft and having a piston head including a first element, a motor coupled to drive a reciprocal longitudinal motion of the piston within the shaft, a pump chamber configured to be removably attached to the pump body and including a rigid wall defining a fluid inlet, a fluid outlet, and an aperture, and a flexible diaphragm fixed across the aperture and including a second element, which mechanically engages the first element when the pump chamber is attached to the pump body so that the reciprocal longitudinal motion of the piston causes alternating stretching and contraction of the flexible diaphragm, thereby modifying a volume of the pump chamber.

BRIEF DESCRIPTION OF THE DRAWINGS

The disclosure is herein described, by way of example only, with reference to the accompanying drawings, wherein.

DETAILED DESCRIPTION OF EMBODIMENTS

In embodiments of the present invention, an infusion pump for a medical system, herein comprising a diaphragm pump, comprises a pump chamber that is removable and disposable, as described hereinbelow. Diaphragm pumps are typically more expensive than other types of infusion pumps (e.g., peristaltic pumps) that are traditionally used in medical systems for delivering irrigation fluid to body tissue during a medical procedure. However, advantages to using a diaphragm pump as an infusion pump (i.e., as opposed to using a peristaltic pump) include less electrical noise and less chance of tubing debris (i.e., due to repeated compression and decompression of tubing in a peristaltic pump) entering the irrigation fluid. By incorporating a pump chamber that can be replaced between medical procedures, diaphragm infusion pumps implementing embodiments of the invention are typically more economical to use than traditional diaphragm pumps.

In embodiments of the present invention, the diaphragm pump comprises a pump body comprising an internal shaft, and a piston disposed within the shaft and having a piston head comprising a first ferromagnetic element. The diaphragm pump also comprises a motor coupled to drive a reciprocal longitudinal motion of the piston within the shaft, and a pump chamber configured to be removably attached to the pump body and comprising a rigid wall defining a fluid inlet, a fluid outlet, and an aperture. As described supra, the pump chamber is disposable, and typically replaced between medical procedures.

The diaphragm pump additionally comprises a flexible diaphragm fixed across the aperture. The flexible diaphragm comprises a second ferromagnetic element, which engages the first ferromagnetic element when the pump chamber is attached to the pump body so that the reciprocal longitudinal motion of the piston causes alternating stretching and contraction of the flexible diaphragm, thereby modifying a volume of the pump chamber.

System Description

Figure 1:
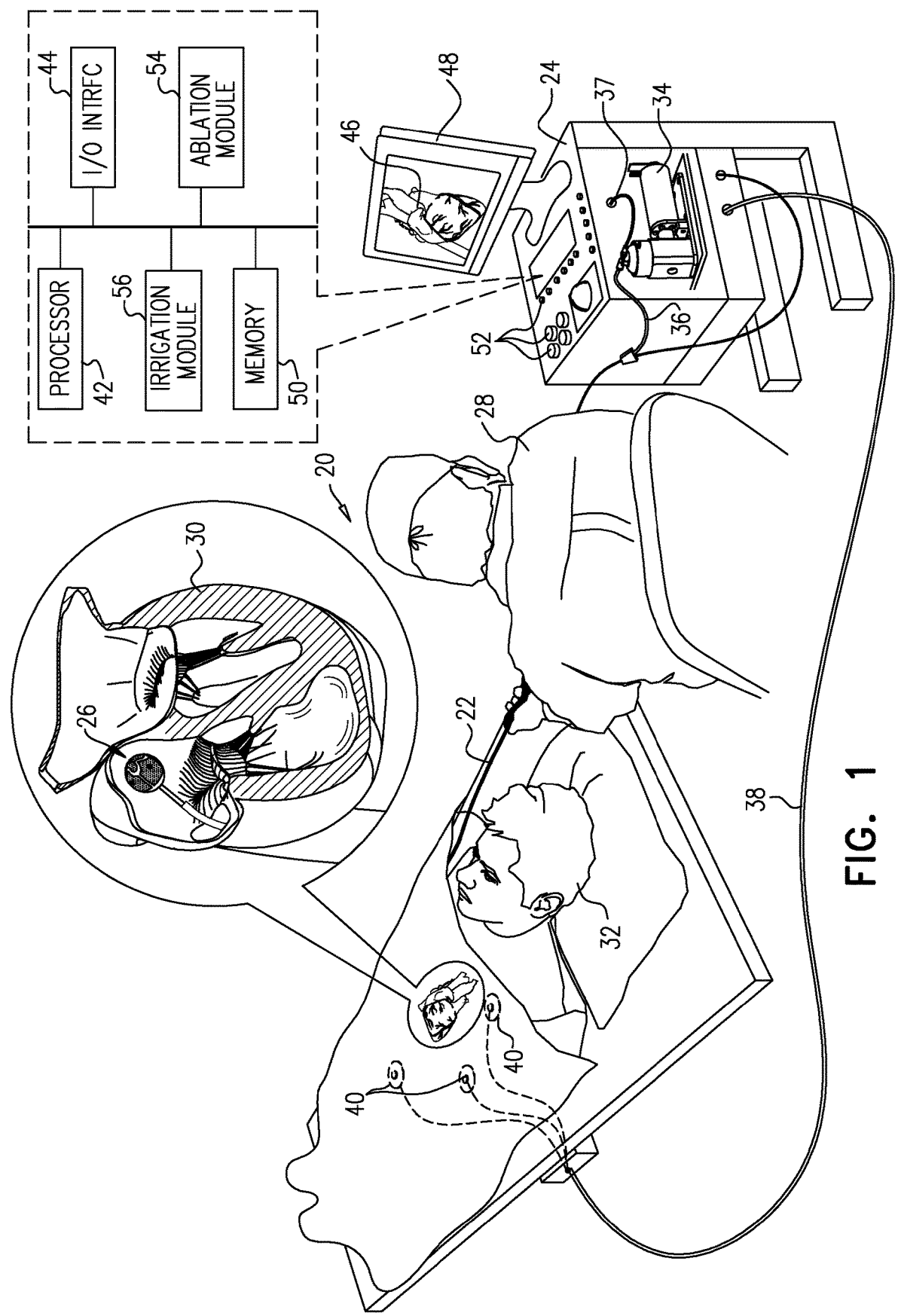
FIG. 1 is a schematic, pictorial illustration of a medical system comprising a diaphragm infusion pump comprising a pump body and a disposable pump chamber, in accordance with an embodiment of the present invention.

FIG. 1 is a schematic, pictorial illustration of a medical system 20 comprising a medical probe 22 and a control console 24, in accordance with an embodiment of the present invention. Medical system 20 may be based, for example, on the CARTO® system, produced by Biosense Webster Inc. (Diamond Bar, Calif., U.S.A.). In the example shown in FIG. 1, medical probe 22 comprises a balloon catheter (also referred to herein as an irrigation catheter) having a distal end 26 that a medical professional 28 can use to perform an ablation procedure on a heart 30 of a patient 32. During the ablation procedure, distal end 26 can irrigate tissue in heart 30 with irrigation fluid (e.g., normal saline solution) that is conveyed from a pump 34 to medical probe 22 via irrigation tubing 36. As described in more detail below, pump 34 receives the irrigation fluid via a pump inlet tubing 37. The irrigation fluid is expelled through irrigation holes (not shown) in distal end 26. In embodiments of the present invention, pump 34 comprises a diaphragm infusion pump that is described in the description referencing FIGS. 2-3 hereinbelow.

Control console 24 is connected, by a cable 38, to body surface electrodes, which typically comprise adhesive skin patches 40 that are affixed to patient 32. Control console 24 comprises a system processor 42 that determines position coordinates of distal end 26 inside heart 30 based on impedances measured between adhesive skin patches 40 and one or more probe electrodes (not shown) that are affixed to distal end 26.

System processor 42 typically comprises a general-purpose computer, with suitable front end and interface circuits for receiving signals from elements of medical probe 22 and controlling the other components of control console 24. Processor 42 may be programmed in software to perform at least one algorithm disclosed herein comprising steps and using features of modules coupled to the processor to perform such steps as set forth herein (e.g., determining position coordinates, as described supra). The software may be downloaded to control console 24 in electronic form, over a network, for example, or it may be provided on non-transitory tangible media, such as optical, magnetic or electronic memory media. Alternatively, some or all of the functions of processor may be carried out by dedicated or programmable digital hardware components.

Although the medical system shown in FIG. 1 uses impedance-based sensing to measure a location of distal end 26, other position tracking techniques may be used (e.g., techniques using magnetic-based sensors). Impedance-based position tracking techniques are described, for example, in U.S. Pat. Nos. 5,983,126, 6,456,864 and 5,944, 022, whose disclosures are incorporated herein by reference. Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. The methods of position sensing described hereinabove are implemented in the above-mentioned CARTO® system and are described in detail in the patents cited above.

Control console 24 also comprises an input/output (I/O) communications interface 44 that enables the control console to transfer signals from, and/or transfer signals to the probe electrodes and adhesive skin patches 40. Based on signals received from the probe electrodes and adhesive skin patches 40, processor 42 can generate a map 46 that shows the position of distal end 26 in the patient's body. During the procedure, processor 42 can present map 46 to medical professional 28 on a display 48, and store data representing the map in a memory 50. Memory 50 may comprise any suitable volatile and/or non-volatile memory, such as random access memory or a hard disk drive. In the configuration shown in FIG. 1, medical professional 28 can manipulate map 46 using one or more input devices 52.

In embodiments of the present invention, distal end 26 comprises one or more ablation electrodes (not shown) that are typically used for tissue ablation. In alternative embodiments, the probe electrodes can also be used for tissue ablation. Control console 24 also comprises an ablation module 54, and an irrigation module 56. Via ablation module 54, processor 42 executes a first given algorithm to monitor and control ablation parameters such as the level and the duration of ablation power (e.g., radio-frequency energy) conveyed to the ablation electrodes. Likewise, via irrigation module 56 (also referred to herein as an irrigation system) coupled to a motor (described below) of pump 34, processor 42 executes a second given algorithm to control the rate of flow of the irrigation fluid (typically between 0-100 milliliters per minute) from pump 34 to medical probe 22.

Figure 2:
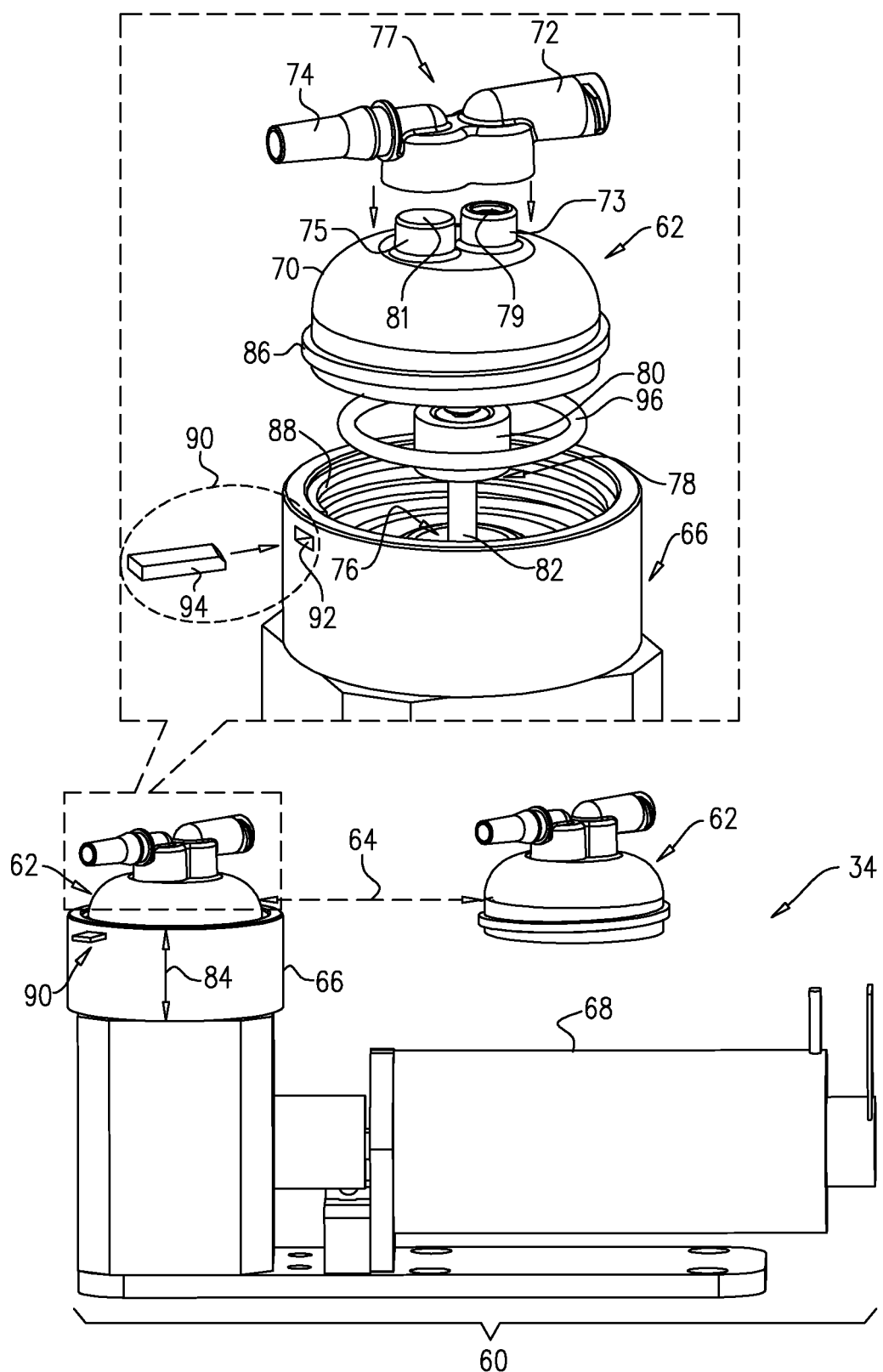
FIG. 2 is a schematic pictorial illustration of the pump body and the disposable pump chamber of the diaphragm infusion pump, in accordance with an embodiment of the present invention.
Figure 3:
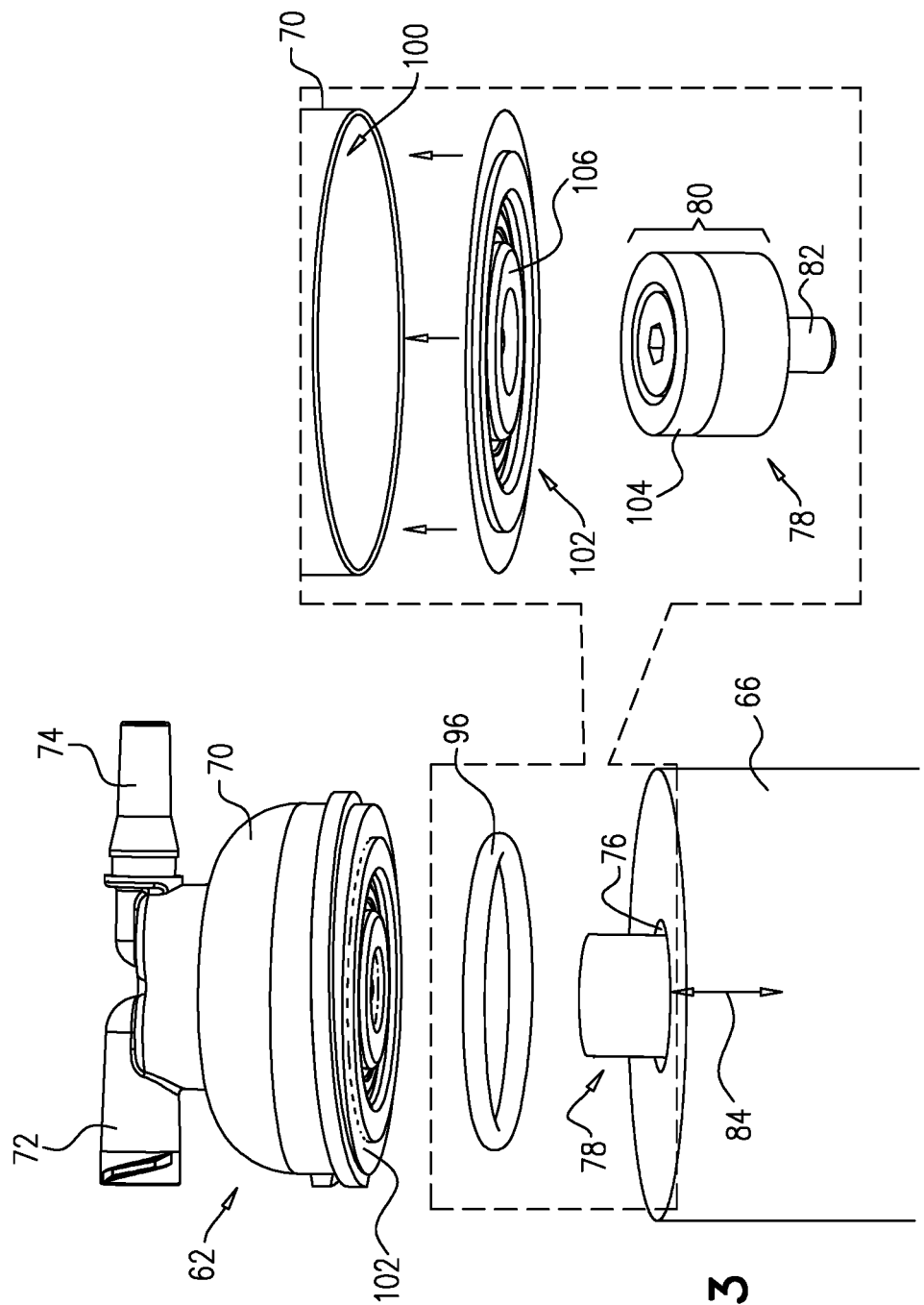
FIG. 3 is a schematic cutaway view of the pump body and the disposable pump chamber, in accordance with an embodiment of the present invention.

FIG. 2 is a schematic pictorial illustration of diaphragm infusion pump 34, and FIG. 3 is a schematic cutaway view of a portion of the pump, in accordance with an embodiment of the present invention. In embodiments of the present invention, diaphragm infusion pump 34 comprises a fixed base unit 60 and a pump chamber 62 that can be removably attached to the base unit, as indicated by a dashed arrow 64. In some embodiments, pump chamber 62 is disposable (i.e., the pump chamber is typically replaced before each medical procedure).

Base unit 60 comprises a pump body 66 and a motor 68. Pump chamber 62 comprises a rigid wall 70 that defines a fluid inlet and a fluid outlet 75. In the example shown in FIG. 2, pump 34 also comprises a fixture 77 that is affixed to pump chamber 62 via fluid inlet 73 and fluid outlet 75. Fixture 77 comprises a first connector 72 that couples fluid inlet 73 to tubing 37, and a second connector 74 that couples fluid outlet 75 to irrigation tubing 36.

Pump chamber 62 comprises one-way valves 79 and 81 that are disposed within fluid inlet 73 and fluid outlet 75, respectively. In operation, one-way valve 79 allows irrigation fluid to flow, via tubing 37 (FIG. 1) and fluid inlet 73, from a fluid reservoir (not shown) into a cavity defined by rigid wall 70, and one-way valve 81 allows the irrigation fluid to flow, via fluid outlet 75, connector 74 and irrigation tubing 36, from the cavity to probe 22.

Pump body 66 comprises a shaft 76 and a piston 78 that is disposed within the shaft and comprises a piston head 80 that is mounted on a first end of a rod 82 that extends through the shaft. Motor 68 is coupled to a second end of rod 82 and drives a reciprocal longitudinal motion (i.e., an oscillation) of piston 78 within shaft 76, as indicated by a solid arrow 84. In embodiments of the present invention, motor 68 comprises any mechanical device that, when coupled to piston 78, oscillates the piston in shaft 76. While embodiments herein describe pump having a simple piston configuration comprising a single piston 78, a diaphragm pump comprising other types of piston configurations is considered to be within the spirit and scope of the present invention.

As described supra, pump chamber 62 is removable and typically disposable. Therefore, in embodiments of the present invention, diaphragm pump 34 comprises a coupling mechanism that enables pump chamber 62 to couple with pump body 66 and enables the pump chamber to uncouple from the pump chamber. In some embodiments, as shown in FIG. 2, the coupling mechanism comprises male and female threadings 86 and 88 on pump chamber 62 and pump body 66, respectively, and a lock 90.

Threadings 86 and 88 mate with each other, thereby enabling pump chamber 62 to be "screwed into" pump body 66. In the example shown in FIG. 2, threading 86 protrudes from pump body 66, and lock 90 comprises a locking keyhole 92 in pump body 34 and a key 94 that fits into the locking keyhole. In operation, upon screwing pump chamber 62 into pump body 66, threading 88 is positioned below keyhole 92, and medical professional 28 (or another individual) can insert key 94 into the keyhole to "lock" pump chamber 62 in place (i.e., to prevent the pump chamber from "unscrewing" from the pump body).

While the example in FIG. 2 shows lock 90 comprising key that is locked into place by threading 86, other types of mechanisms for locking pump chamber 62 to pump body 66 are considered to be within the spirit and scope of the present invention. For example, lock 90 may include a spring that drives key 94 through keyhole 92 into an indentation in rigid wall 70, thereby locking pump chamber 62 to pump body 66.

In some embodiments, diaphragm pump 34 may comprise an O-ring 96 that is mounted between pump chamber 62 and pump body 66. O-ring 96 can be configured to apply pressure (e.g., like a spring) to pump chamber 62 in order to reinforce the locking of the pump chamber to pump body 66.

FIG. 3 is a schematic cutaway view of pump chamber 62 and pump body 66. For purposes of visual simplicity, the upper portion of the pump body comprising threading 88 is not shown in FIG. 3. Rigid wall 70 defines an aperture 100 at the bottom of pump chamber 62, and a flexible diaphragm 102 is fixed across the aperture. Examples of materials that can be used for diaphragm 102 include, but are not limited to, silicon-based and polyurethane-based materials. In some embodiments, diaphragm 102 may comprise a plastic ring (not shown) that can be affixed to rigid wall 70 (i.e., at aperture 100) using glue or other types of adhesion methods (e.g., an ultrasonic adhesive). In alternative embodiments, rigid wall 70 may comprise a mechanical mechanism that, when diaphragm 102 is pressed against aperture 100, engages the plastic ring in order to lock the diaphragm into place.

In embodiments of the present invention, piston head 80 comprises a first ferromagnetic element 104, and flexible diaphragm 102 comprises a second ferromagnetic element 106. In one embodiment, first ferromagnetic element 104 comprises a permanent magnet and second ferromagnetic element 106 comprises a metal with ferromagnetic properties. In another embodiment, first ferromagnetic element 104 comprises a metal with ferromagnetic properties and second ferromagnetic element 106 comprises a permanent magnet. In an additional alternative embodiment, elements 104 and 106 are both permanent magnets. In a further embodiment, elements 104 and/or 106 may comprise electromagnets.

While the example shown in FIGS. 2 and 3 uses ferromagnetic elements 104 and 106 to engage piston head 80 to diaphragm 102, other methods of engaging the piston head to the diaphragm are considered to be within the spirit and scope of the present invention. For example, piston head 80 may comprise a first element (e.g., a pin), and diaphragm 102 may comprise a second element (e.g., a slot) that is configured to mechanically engage the first element when pump chamber 62 is attached to pump body 66.

In embodiments of the present invention, due to magnetic attraction between first ferromagnetic element 104 and second ferromagnetic element 106, the first ferromagnetic element engages the second ferromagnetic element when pump chamber 62 is attached to pump body 66, so that reciprocal longitudinal motion 84 of piston 78 causes alternating stretching and contraction of flexible diaphragm 102. The stretching and the contracting of flexible diaphragm 102 modifies a volume of the pump chamber, thereby drawing irrigation fluid into the pump chamber via connector 72 and fluid inlet 73, and pumping the irrigation fluid from the chamber via fluid outlet 75 and connector 74.

In some embodiments, dimensions of pump chamber 62 (and therefore the volume of the pump chamber) enable diaphragm infusion pump 34 to be self-priming. In these embodiments, the volume of irrigation fluid that enters pump chamber 62 during the (reciprocal longitudinal) motion of piston 78 that pulls diaphragm 102 away from pump chamber 62 is in accordance with the volume of irrigation fluid that exits fluid outlet 75 when the motion of the piston pushes the diaphragm towards fixture 77.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
a pump body comprising an internal shaft, a first threading, and a keyhole;
a key configured to fit into the keyhole;
a piston disposed within the internal shaft and having a piston head comprising a first ferromagnetic element;
a motor coupled to drive a reciprocal longitudinal motion of the piston within the internal shaft;
a pump chamber comprising a fluid inlet, a fluid outlet, a second threading that mates with the first threading, and an aperture; and
a flexible diaphragm fixed across the aperture and comprising a second ferromagnetic element, which engages the first ferromagnetic element when the pump chamber is attached to the pump body so that the reciprocal longitudinal motion of the piston causes alternating stretching and contraction of the flexible diaphragm, thereby modifying a volume of the pump chamber.

2. The apparatus according to claim 1, wherein the first ferromagnetic element comprises a permanent magnet, and wherein the second ferromagnetic element comprises a metal with ferromagnetic properties.

3. The apparatus according to claim 1, and comprising an irrigation catheter coupled to the fluid outlet.

4. The apparatus according to claim 1, wherein the pump chamber is disposable.

5. The apparatus according to claim 1, wherein a pump defined by the pump chamber and the flexible diaphragm is self-priming.

6. An apparatus, comprising:
a pump body comprising an internal shaft, a first threading, and a keyhole;
a key configured to fit into the keyhole;
a piston disposed within the internal shaft and having a piston head comprising a first element;
a motor coupled to drive a reciprocal longitudinal motion of the piston within the internal shaft;
a pump chamber comprising a fluid inlet, a fluid outlet, a second threading that mates with the first threading, and an aperture; and
a flexible diaphragm fixed across the aperture and comprising a second element, which mechanically engages the first element when the pump chamber is attached to the pump body so that the reciprocal longitudinal motion of the piston causes alternating stretching and contraction of the flexible diaphragm, thereby modifying a volume of the pump chamber.

* * * * *